United States Patent [19] … [11] 4,008,604
Roach et al. … [45] Feb. 22, 1977

[54] DETERMINATION OF CARBON ANALYSIS IN IRONS

[75] Inventors: Maurice P. Roach; Ann E. Schoenjahn; Larry G. Carmack, all of Waterloo, Iowa

[73] Assignee: Deere & Company, Moline, Ill.

[22] Filed: Apr. 7, 1976

[21] Appl. No.: 674,427

[52] U.S. Cl. .............................. 73/17 R; 75/130 R
[51] Int. Cl.² ........................................ G01N 25/02
[58] Field of Search ............... 73/17 R, 359; 75/60, 75/130 R

[56] References Cited
UNITED STATES PATENTS

| | | |
|---|---|---|
| 3,375,106 | 3/1968 | McKissick et al. ................ 75/130 |
| 3,546,921 | 12/1970 | Bourke et al. ...................... 73/17 |
| 3,891,834 | 6/1975 | Warinski ........................... 73/17 |

Primary Examiner—Herbert Goldstein

[57] ABSTRACT

A new, accurate method for the determination of percent total carbon in a molten hypoeutectic or hypereutectic iron is disclosed. It has been found that percent total carbon content of a molten iron is related to a straight-line function of the difference in liquidus and eutectoid transformation (i.e., austenite to pearlite) temperatures of the iron. A standard liquidus - eutectoid transformation temperature difference (based on total carbon content) is generated. A molten iron sample is cooled through the eutectoid transformation temperature and the difference in the liquidus and eutectoid transformation temperatures is compared with the standard liquidus-eutectoid transformation temperature difference to determine the percent total carbon of the sample.

10 Claims, 1 Drawing Figure

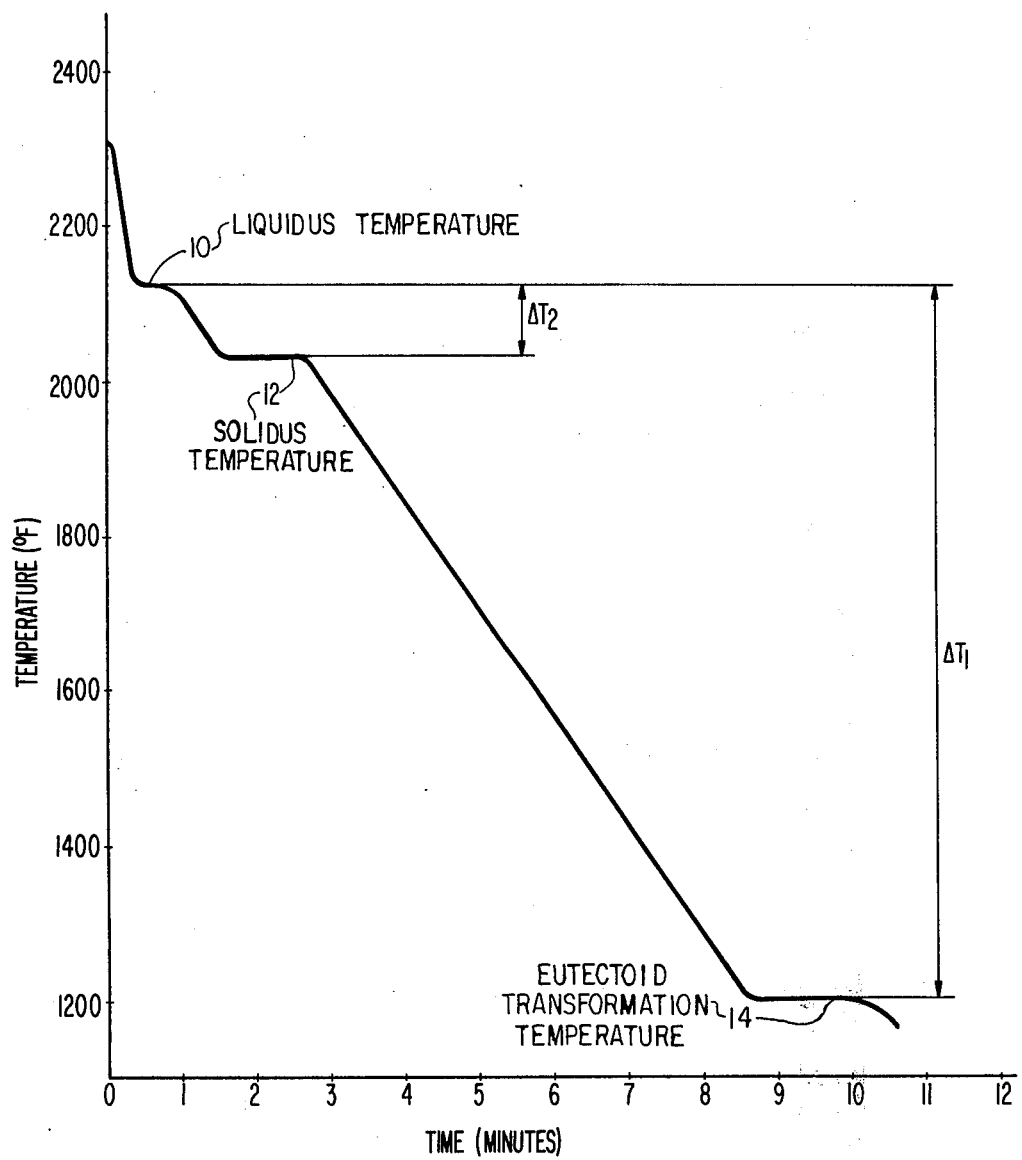

DETERMINATION OF CARBON ANALYSIS IN IRONS

BACKGROUND OF THE INVENTION

The carbon content of molten iron is an important variable in iron foundry production since the amount of carbon has an important effect on the mechanical and metallurgical properties of the final iron product.

Generally the carbon content of molten iron may be determined, prior to casting of the iron, by chemical analysis or by thermal analysis. Chemical analysis is generally too slow for production facilities and essentially all production facilities use thermal analysis for the determination of the carbon equivalent of molten iron.

In the past, thermal analysis has involved the determination of the carbon equivalent of molten hypoeutectic iron (which carbon equivalent may be defined as the total carbon percent plus one-third of the total silicon content plus one-third of the total phosphorous content) by generating a cooling curve for the molten iron sample and noting the liquidus thermal arrest temperature (which is the temperature at which austenite starts to precipitate in the sample). The carbon equivalent-cooling curve technique is described, for example, in an article "Carbon Equivalent in Sixty Seconds," Modern Casting Magazine, March, 1962, pages 37 to 39. As noted therein, the liquidus break for hypereutectic irons (those with carbon equivalents above 4.3 weight percent) is not clear enough so this method is limited to hypoeutectic irons.

A method of utilizing thermal analysis of this type for hypereutectic irons is disclosed in U.S. Pat. No. 3,546,921, which discloses treating the molten sample (as by coating the sample cup) with a carbide stabilizer (e.g., bismuth, boron, lead, magnesium, cerium or mischmetal) which retards primary graphite formation in the iron during solidification to insure an arrest at the liquidus temperature. The carbon equivalent of the hypereutetic iron can then be determined by comparison of the initial arrest temperature with a reference chart based on samples which have been chemically analyzed and the carbon equivalent determined. The amount of carbon and silicon in the cast iron determines the physical properties and microstructure of the iron. When the carbon equivalent is determined by thermal analysis, the silicon content is measured by wet or spectrographic analysis (or by calculation if the total carbon content is known). Thus, two analyses are generally required to determine the carbon and silicon content.

The use of a cooling curve computer for detecting the liquidus and solidus temperatures of molten iron samples and computing the carbon equivalent therefrom by means of an empirical equation is disclosed in U.S. Pat. No. 3,891,834. If desired, the computer may also be utilized to store a signal representing the eutectoid temperature which may then be utilized to determine the percent silicon by another empirical equation. The percent carbon can be determined from the computed carbon equivalent and percent silicon values (assuming phosphorous as zero).

A need remains for an accurate, rapid method for the determination of total percent carbon in a molten iron sample which does not require either an initial determination of the carbon equivalent or a computer and which is applicable to both hypoeutectic and hypereutectic irons.

OBJECTS AND SUMMARY OF THE INVENTION

It is an object of this invention to provide a method for the thermal analysis of molten iron samples to measure the total carbon percent of the sample which avoids or alleviates the problems of the prior art.

It is further an object of this invention to provide a rapid, accurate thermal analysis for the total carbon content of a molten iron sample which is appliable to both hypoeutectic and hypereutectic iron.

Another object of this invention is to provide a thermal analysis method for the determination of total carbon content in malleable, gray and ductile irons.

A further object of this invention is to provide a rapid, accurate method for the direct thermal analysis of molten iron to determine total carbon content which does not require the determination of the carbon equivalent of the sample.

In one aspect, the present invention provides a method for determining the total carbon content of carbon-containing iron which comprises:

allowing samples of molten iron of known total carbon content to cool at least through the first eutectoid transformation temperature;

determining the temperature difference between the liquidus and first eutectoid transformation temperature for each of the said samples of known total carbon content;

determining a standard liquidus-first eutectoid transformation temperature difference with respect to carbon content;

allowing a sample of iron of unknown total carbon content to cool at least through the first eutectoid transformation temperature;

determining the liquidus-first eutectoid transformation temperature difference for the sample of unknown total carbon content; and comparing the resulting liquidus-first eutectoid transformation temperature difference for the sample of unknown total carbon content with the standard liquidus-first eutectoid transformation.

In another aspect, the present invention provides a method for directly determining the percent total carbon of a molten iron sample which comprises cooling said sample;

detecting the liquidus and eutectoid temperatures of said cooled sample to obtain a value representing the difference in said temperatures; and comparing the value obtained with a reference standard of liquidus-eutectoid temperature differences based on percent total carbon content to obtain the percent total carbon of the said sample.

The process of the present invention is based on the discovery that a relationship exists between the percent total carbon content of a molten iron sample and the difference in the liquidus and eutectoid temperatures of the sample. Once the relationship is established, the percent total carbon of an unknown sample can be readily determined by cooling the sample, detecting the liquidus-eutectoid temperature difference and comparing the detected difference to the established standard relationship. The percent total carbon can thus be directly established. In addition, the utilization of the eutectoid temperature instead of the solidus temperature imparts a greater temperature difference which imparts a higher degree of accuracy to the method. The process of the present invention is also readily adaptable for use with available temperature recording devices or with more highly computerized systems, if desired.

Unless otherwise indicated, all percentages, portions and amounts are by weight and all temperatures are expressed as degrees Fahrenheit.

BRIEF DESCRIPTION OF THE DRAWING

The FIGURE is a cooling curve or graph of temperature against time for a typical cast iron sample.

DETAILED DESCRIPTION OF THE INVENTION

The Figure shows a typical cooling curve obtained by cooling a molten cast iron sample. Such curves can be obtained from commercially available recording devices which are operatively connected to known molten metal receiving devices such as described, for example, in U.S. Pat. No. 26,409 or the aforesaid Modern Castings article. Such devices and system are well-known in the art and any such suitable system may be utilized with the present invention.

As may be seen in the Figure, the molten sample begins cooling as soon as it is poured into the metal receiving device with an installed thermocouple (or sample cup). At point 10, the slope of the cooling curve becomes approximately zero and a first thermal arrest occurs. This point 10 corresponds to the liquidus temperature of the molten iron. The iron sample begins cooling again (generally at a slower rate) until a second thermal arrest 12 occurs which corresponds to the solidus temperature. The sample begins cooling again unitl a third thermal arrest 14 occurs which corresponds to the first eutectoid transformation (i.e., the austenite to pearlite transformation). The temperature difference $\Delta T_1$ between the liquidus temperature and the eutectoid temperature for a given sample may then be utilized to determine the percent total carbon content of the sample from a standard relationship as described hereinbelow. As may be seen from the Figure, $\Delta T_1$ is considerably larger than the temperature difference $\Delta T_2$ between the liquidus temperature and solidus temperature which temperature difference $\Delta T_2$ is conventionally utilized to calculate the carbon equivalent of a given sample. This great difference in $\Delta T_1$ imparts a greater degree in accuracy in both measuring the difference and in the ultimate carbon value obtained from the difference.

The standard relationship between $\Delta T_1$ and percent total carbon content may be obtained by cooling a number of molten iron samples, determining the individual $\Delta T_1$ values for each sample and determining the total carbon content for each sample by conventional chemical analysis. Analysis of these values (as by linear regression analysis) yields an algebraic linear equation which can be represented as a straight line on a graph of the form:

$$\% \text{ Total Carbon} = m (\Delta T) + b \qquad (1)$$

where $m$ is a constant, $\Delta T$ is the difference in degrees Fahrenheit between the liquidus temperature and the eutectoid temperature (or $\Delta T_1$ as described above) and $b$ is a constant.

For unalloyed cast iron, the equation has been found to be:

$$\% \text{ Total Carbon} = -0.004265 (\Delta T) + 7.000 \qquad (2)$$

When the iron is alloyed, the constants will be changed slightly but the same determination can be used to provide an accurate relationship for any given amount of alloying agent.

The percent total carbon of a given sample, after the liquidus and eutectoid temperatures (in degrees Fahrenheit) are measured, can be obtained by inserting $\Delta T_1$ (the difference between the liquidus and eutectoid temperatures) into equation (2) and arithmetically calculating the result. For convenience purposes, particularly for use in a production environment, the relationship can be expressed at a table, chart or graph to facilitate the obtaining of the percent total carbon. In addition, the process of the present invention may be incorporated with suitable computerized systems to provide machine computations of the total carbon content.

The process of the present invention may be utilized to determine the percent total carbon in hypereutectic, eutectic and hypoeutectoid cast irons including specifically gray irons, ductile irons and malleable irons. The irons may also contain alloying elements such as silicon, magnesium, nickel, chromium, copper and molybdenum. Although, as noted above, the constants in the linear equation (1) will vary somewhat for each alloying element, the same procedure may be used to determine the particular algebraic linear relationship for the alloyed iron and percent total carbon content. Also, the liquidus-solidus temperature difference ($\Delta T_2$) observed during cooling of the sample may be utilized to determine the carbon equivalent of the sample in accordance with known techniques. Once the carbon equivalent and total carbon content have been determined, the silicon content may be determined from the equation (assuming phosphorous is zero):

$$\text{Carbon Equivalent} = \text{Total Carbon} + \frac{1}{3} \text{ Total Silicon} \qquad (3)$$

Thus, the process of the present invention allows rapid and accurate determination of both carbon and silicon in the same operation without the necessity for further analysis. Any adjustment in the carbon or silicon content of the melt can then readily be made in accordance with well-known techniques.

The invention is additionally illustrated in connection with the following Example which is to be considered as illustrative of the present invention. It should be understood, however that the invention is not limited to the specific details of the Example.

EXAMPLE

Samples of molten, unalloyed iron of varying carbon content are poured into a conventional sample cup containing a thermocouple which is operatively connected to a conventional temperature recording device which provides a chart (or cooling curve) of temperature against time. The samples are cooled through the eutectoid transformation (i.e., austenite to pearlite) temperature. The liquidus and eutectoid temperatures for each sample is obtained from the cooling curve and the difference in these temperatures (or $\Delta T$) for each sample is calculated. Each sample is also chemically analyzed to obtain the percent carbon content. Typical values obtained are as follows:

| ΔT° | % Total Carbon |
|---|---|
| 818 | 3.50 |
| 824 | 3.49 |
| 832 | 3.44 |
| 842 | 3.41 |
| 856 | 3.35 |
| 860 | 3.33 |

By linear regression analysis, a straight-line equation is derived for the percent total carbon which equation is $$\% \text{ Total Carbon} = 0.004265 \, (\Delta T) + 7.00$$

Further samples are cooled as described above and the $\Delta T$ values obtained from the cooling curve. The % total carbon content of these samples is then obtained from the above equation. Chemical analysis of these samples for percent total carbon content shows that the values obtained from the equation are accurate to within ± 0.04%. In comparison, values of carbon equivalent obtained from the difference in liquidus and solidus temperatures with charts generally used in foundry production are accurate only to within ± 0.10%.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed:

1. A method for determining the total carbon content of carbon-containing iron which comprises:
   allowing samples of molten iron of known total carbon content to cool at least through the first eutectoid transformation temperature;
   determining the temperature difference between the liquidus and first eutectoid transformation temperature for each of the said samples of known total carbon content;
   determining a standard liquidus-first eutectoid transformation temperature difference with respect to carbon content;
   allowing a sample of iron of unknown total carbon content to cool at least through the first eutectoid transformation temperature;
   determining the liquidus-first eutectoid transformation temperature difference for the said sample of unknown total carbon content; and
   comparing the resulting liquidus-first eutectoid transformation temperature difference for the sample of unknown total carbon content with the standard liquidus-first eutectoid transformation temperature difference to determine the total carbon content thereof.

2. The method of claim 1 wherein the molten iron is a hypereutectic iron.

3. The method of claim 1 wherein the molten iron is a hypoeutectic iron.

4. A method for directly determining the percent total carbon of a molten iron sample which comprises cooling said sample;
   detecting the liquidus and eutectoid temperatures of said cooled sample and obtaining a value representing the difference in said temperatures; and
   comparing the value obtained with a reference standard of liquidus-eutectoid temperature differences based on percent total carbon content to obtain the percent total carbon of the said sample.

5. The method of claim 4 wherein said molten iron is an unalloyed iron.

6. The method of claim 5 wherein said reference standard is derived from the equation $$\% \text{ Total Carbon} = -0.004265 \, (\Delta T) + 7.000$$

where $\Delta T$ is the difference in degrees Fahrenheit between the liquidus temperature and the eutectoid temperature.

7. The method of claim 4 wherein the iron is a hypoeutectic iron.

8. The method of claim 4 wherein the iron is a hypereutectic iron.

9. The method of claim 4 wherein the reference standard is obtained by linear regression analysis of liquidus-eutectoid temperature differences of iron samples of determined carbon content.

10. The method of claim 4 wherein the reference standard is expressed in the form of a table, chart or graph.

* * * * *